(12) United States Patent
Wang et al.

(10) Patent No.: US 10,799,375 B2
(45) Date of Patent: Oct. 13, 2020

(54) AORTIC BARE STENT AND AORTIC DISSECTION STENT

(71) Applicant: HANGZHOU WEIQIANG MEDICAL TECHNOLOGY CO., LTD., Hangzhou (CN)

(72) Inventors: Yongsheng Wang, Hangzhou (CN); Weiguo Fu, Hangzhou (CN); Jianmin Li, Hangzhou (CN); Tingchao Zhang, Hangzhou (CN)

(73) Assignee: HANGZHOU WEIQIANG MEDICAL TECHNOLOGY CO., LTD., Hangzhou (CN)

( * ) Notice: Subject to any disclaimer, the term of this patent is extended or adjusted under 35 U.S.C. 154(b) by 102 days.

(21) Appl. No.: 16/084,264

(22) PCT Filed: Mar. 16, 2017

(86) PCT No.: PCT/CN2017/076942
§ 371 (c)(1),
(2) Date: Sep. 12, 2018

(87) PCT Pub. No.: WO2017/157320
PCT Pub. Date: Sep. 21, 2017

(65) Prior Publication Data
US 2019/0070027 A1    Mar. 7, 2019

(30) Foreign Application Priority Data
Mar. 18, 2016 (CN) .......................... 2016 1 0158220

(51) Int. Cl.
*A61F 2/07* (2013.01)
*A61F 2/88* (2006.01)
(Continued)

(52) U.S. Cl.
CPC .................. *A61F 2/88* (2013.01); *A61F 2/07* (2013.01); *A61F 2/89* (2013.01); *A61F 2/915* (2013.01);
(Continued)

(58) Field of Classification Search
CPC .. A61F 2/07; A61F 2/915; A61F 2002/91525; A61F 2002/91541;
(Continued)

(56) References Cited

U.S. PATENT DOCUMENTS 5,366,504 A * 11/1994 Andersen .................. A61F 2/04
606/194
6,033,433 A * 3/2000 Ehr ........................... A61F 2/91
623/1.16
(Continued)

FOREIGN PATENT DOCUMENTS

CN    1331957 A    1/2002
CN    1681555 A    10/2005
(Continued)

OTHER PUBLICATIONS

European Search Report issued in corresponding European Patent Application No. 17765862.2, dated Aug. 1, 2019.
(Continued)

*Primary Examiner* — Paul B Prebilic
(74) *Attorney, Agent, or Firm* — Cooper Legal Group, LLC

(57) ABSTRACT

An aortic bare stent and an aortic dissection stent are disclosed. The aortic bare stent is in a tubular net structure, with multiple support stents in circles and arranged along an axial direction. Two adjacent support stents are connected by a connector stent. The connector stent is made of a hyperelastic material. A flexural rigidity of the connector stent is less than that of the support stent. The support stent is made
(Continued)

of a single-strand hyper-elastic nickel titanium wire or formed by cutting a nickel titanium tubing. The connector stent is made of a multi-strand composite wire. The multi-strand composite wire is formed by twisting or weaving multiple strands of filaments, and each strand of filament is independently of a nickel titanium material.

20 Claims, 17 Drawing Sheets

(51) Int. Cl.
*A61F 2/915* (2013.01)
*A61F 2/89* (2013.01)
*A61F 2/92* (2013.01)
*A61F 2/95* (2013.01)
*A61F 2/90* (2013.01)

(52) U.S. Cl.
CPC .................. *A61F 2/92* (2013.01); *A61F 2/95* (2013.01); *A61F 2/90* (2013.01); *A61F 2002/91558* (2013.01); *A61F 2002/9511* (2013.01); *A61F 2210/0014* (2013.01); *A61F 2220/0075* (2013.01); *A61F 2250/0018* (2013.01); *A61F 2250/0029* (2013.01); *A61F 2310/00023* (2013.01)

(58) Field of Classification Search
CPC .... A61F 2002/9155; A61F 2002/91583; A61F 2002/91558; A61F 2210/0014; A61F 2220/0075; A61F 2250/0018; A61F 2250/0029; A61F 2250/0036
USPC ........................................................ 623/1.22
See application file for complete search history.

(56) References Cited

U.S. PATENT DOCUMENTS

| | | | | |
|---|---|---|---|---|
| 6,190,403 | B1* | 2/2001 | Fischell | A61F 2/91 623/1.16 |
| 6,193,747 | B1* | 2/2001 | von Oepen | A61F 2/91 623/1.15 |
| 6,231,598 | B1* | 5/2001 | Berry | A61L 31/022 623/1.15 |
| 6,241,757 | B1* | 6/2001 | An | A61F 2/90 623/1.1 |
| 6,331,188 | B1* | 12/2001 | Lau | A61F 2/92 623/1.13 |
| 7,029,493 | B2* | 4/2006 | Majercak | A61F 2/91 606/194 |
| 7,326,239 | B1 | 2/2008 | Fedida | |
| 7,854,756 | B2* | 12/2010 | Shaw | A61F 2/90 623/1.15 |
| 2001/0032010 | A1 | 10/2001 | Hoover | |
| 2002/0007211 | A1* | 1/2002 | Pinchasik | A61F 2/915 623/1.16 |
| 2003/0055484 | A1 | 3/2003 | Maroney | |
| 2003/0069630 | A1 | 4/2003 | Burgermeister | |
| 2003/0208260 | A1 | 11/2003 | Lau | |
| 2004/0176832 | A1 | 9/2004 | Hartley et al. | |
| 2006/0142836 | A1* | 6/2006 | Hartley | A61F 2/95 623/1.11 |
| 2009/0043371 | A1 | 2/2009 | Fearnot | |
| 2010/0070024 | A1* | 3/2010 | Venturelli | A61F 2/915 623/1.22 |
| 2010/0076543 | A1 | 3/2010 | Melsheimer et al. | |
| 2011/0224777 | A1 | 9/2011 | Von Oepen et al. | |
| 2013/0211489 | A1 | 8/2013 | Makower et al. | |

FOREIGN PATENT DOCUMENTS

| | | |
|---|---|---|
| CN | 101636130 A | 1/2010 |
| CN | 103767805 A | 5/2014 |
| CN | 104602647 A | 5/2015 |
| CN | 205612592 U | 10/2016 |
| JP | 2002291904 A | 10/2002 |

OTHER PUBLICATIONS

International search report issued in corresponding international application No. PCT/CN2017/076942 dated Jun. 20, 2017.

* cited by examiner

AORTIC BARE STENT AND AORTIC DISSECTION STENT

TECHNICAL FIELD

The present disclosure relates to the field of medical instrument, and particularly to an aortic bare stent and an aortic dissection stent.

BACKGROUND

An aorta blood vessel of a human body is constituted by three tunicas, namely, a tunica intima, a tunica media, and a tunica adventitia, respectively, and the three tunicas fit closely and together support pass-through of blood.

An aortic dissection occurs when the tunica intima is locally torn, and the tunica intima is gradually dissected and expanded under powerful blood impacts, thus forming two lumens, i.e., a true lumen and a false lumen, inside an artery. The aortic dissection is a cardiovascular disease seriously threatening life health of human beings, with an overall morbidity of about 50/100 thousand, and a fatality rate of about 15/100 thousand.

Stanford classification is a relatively common classification for aortic dissections. The Stanford classification is divided into two types, type A and type B, where a Stanford type A dissection refers to a dissection involving an ascending aorta and/or an aortic arch; a Stanford type B dissection refers to a dissection merely involving a descending thoracic aorta.

The Stanford type A dissection currently is still treated through conventional surgical operations due to a special anatomical structure of a lesion position; the Stanford type B dissection currently is mainly subjected to endovascular interventional treatment, which has been in quite rapid development in recent years.

SUMMARY

The present disclosure provides an aortic bare stent, which has a proper radial support strength, a proper axial support strength, and a good bending flexibility, moreover, when being released, the aortic bare stent is easy to be bent to be adapted to a shape of a blood vessel, thereby reducing compression to a blood vessel wall.

An aortic bare stent is in a tubular net structure, with multiple support stents in circles and arranged along an axial direction. Two adjacent support stents are connected by a connector stent. The connector stent is made of a hyper-elastic material, and a flexural rigidity of the connector stent is less than that of the support stent.

The flexural rigidity of the support stent is larger than that of the connector stent. The support stent ensures that the aortic bare stent has a sufficient support strength in a radial direction. The connector stent ensures that the aortic bare stent has a good bending flexibility, and meanwhile also can serve a function of axial support.

The support stent and the connector stent are all self-expanding stents. In a natural extension state, since the support stent and the connector stent all have a certain flexural rigidity, a straight-tube-shape form of the aortic bare stent can be maintained.

When the aortic bare stent according to the present disclosure is bent under an external stress, the connector stent is deformed, so as to be adapted to overall bending of the aortic bare stent, and after the external stress disappears, the connector stent can restore an initial shape, that is, the aortic bare stent turns back to the straight-tube shape in a natural extension state.

In the present disclosure, the support stent and the connector stent serve different functions. The support stent is mainly used to provide a radial support function, and can well abut against a blood vessel. The connector stent, on one hand, needs to maintain the straight-tube-shape form of the aortic bare stent, and on the other hand, further needs to be easily deformed under an external force, such that the aortic bare stent has a good flexibility.

Since the support stent and the connector stent serve different functions, the support stent and the connector stent have different flexural rigidities, preferably, a ratio of the flexural rigidity of the connector stent to the flexural rigidity of the support stents falls within a range of 0.5:100~20:100.

It is hard to measure the flexural rigidity of the connector stent and the flexural rigidity of the support stent, respectively. Since the connector stent and the support stent are similar in shapes, the flexural rigidity of the connector stent and the flexural rigidity of the support stent may be measured according to performances of materials for forming the connector stent and the support stent, respectively.

In the present disclosure, the flexural rigidity of the connector stent is defined as a flexural rigidity of the aortic bare stent fabricated completely by the material of the connector stent; the flexural rigidity of the support stent is defined as a flexural rigidity of the aortic bare stent fabricated completely by the material of the support stent.

When the flexural rigidity of the support stent and the flexural rigidity of the connector stent are compared, structure parameters of the aortic bare stent, for example, a radial dimension, an axial length, and so on, are the same, but excluding contents belonging to properties of the materials themselves, such as a cross section area of the materials, and so on.

Preferably, the support stent is made of a single-strand hyper-elastic nickel titanium wire or formed by cutting a nickel titanium tubing.

Fabricating the support stent by the hyper-elastic nickel titanium wire in the related art aims at ensuring the proper flexural rigidity of the support stent.

The flexural rigidity reflects a capability that a structure resists bending deformation. A formula for calculating the flexural rigidity of a structure in mechanics of materials is EI, where E is an elasticity modulus of a material, which is a constant; I is an inertial moment of a cross section of the material, and the inertial moment I of the cross section of a circular shape is $\pi d^4/64$, where d is a wire diameter (in the present disclosure, the wire diameter refers to a diameter of a cross section of the nickel titanium wire unless otherwise stated). Therefore, with the same nickel titanium wire, the flexural rigidity is proportional to the wire diameter to the power of four. The smaller the wire diameter of the nickel titanium wire is, the smaller the flexural rigidity is, and the bigger the bending deformation allowed is. For example, the flexural rigidity of the nickel titanium wire with the wire diameter of 0.3 mm is 337 times that of the nickel titanium wire with the wire diameter of 0.07 mm.

Preferably, the hyper-elastic nickel titanium wire for fabricating the support stent has a diameter falling within a range of 0.2~0.45 mm. Further preferably, the hyper-elastic nickel titanium wire for fabricating the support stent has a diameter falling within a range of 0.3~0.4 mm. Most preferably, the hyper-elastic nickel titanium wire for fabricating the support stent has a diameter of 0.3 mm.

Preferably, the connector stent is made of a multi-strand composite wire, the multi-strand composite wire is formed by twisting or weaving multiple strands of filaments, and each strand of filament is independently of a nickel titanium material or a polymer material.

Preferably, each strand of filament of the multi-strand composite wire is a hyper-elastic nickel titanium filament. Compared with a single nickel titanium filament with the same diameter, the multi-strand composite wire not only allows a relatively big bending deformation to increase the bending flexibility of the aortic bare stent, but also has a certain strength, thus ensuring radial and axial support performances of the aortic bare stent.

In the multi-strand composite wire, there is at least one hyper-elastic nickel titanium filament, and the remaining strands of filaments may be hyper-elastic polymer fibers, polymer sutures or mix-woven polymer sutures, for example, PET sutures, PP sutures, and so on.

Preferably, the multi-strand composite wire is formed by twisting or weaving 2~7 strands of filaments. For example, the multi-strand composite wire is formed by twisting or weaving three strands of filaments. Alternatively, the multi-strand composite wire is formed by twisting or weaving four strands of filaments. Alternatively, the multi-strand composite wire is formed by twisting or weaving five strands of filaments. Alternatively, the multi-strand composite wire is formed by twisting or weaving six strands of filaments.

The flexural rigidity of the connector stent depends on the structure of the connector stent, and the material for fabricating the connector stent. The material of the connector stent is a multi-strand composite wire. A filament diameter of each strand of filament of the multi-strand composite wire affects the flexural rigidity of the connector stent. In order to obtain the proper flexural rigidity, preferably, each strand of filament of the multi-strand composite wire has a diameter falling within a range of 0.05~0.2 mm. Further preferably, each strand of filament of the multi-strand composite wire has a diameter falling within a range of 0.07~0.10 mm. Further preferably, each strand of filament of the multi-strand composite wire has a diameter falling within a range of 0.07~0.08 mm. Most preferably, each strand of filament of the multi-strand composite wire has a diameter of 0.07 mm.

Preferably, the multi-strand composite wire is formed by twisting three strands of hyper-elastic nickel titanium filaments, and each strand of the hyper-elastic nickel titanium filament has a filament diameter of 0.07 mm.

Preferably, the multi-strand composite wire is formed by weaving three strands of hyper-elastic nickel titanium filaments, and each strand of the hyper-elastic nickel titanium filament has a filament diameter of 0.07 mm.

If the multi-strand composite wire is formed by twisting the hyper-elastic nickel titanium filaments, the twisted multi-strand nickel titanium wire has a wire diameter (a diameter of a circumscribed circle of a cross section) less than or equal to that of the support stent. Preferably, the twisted multi-strand nickel titanium wire has the wire diameter of 0.15 mm.

The aortic bare stent according to the present disclosure is in the straight-tube shape in the natural extension state, and after being release in vivo, the aortic bare stent is bent, and extends at equal diameters or variable diameters along a length direction of the straight-tube shape, so as to be adapted to the shape of the blood vessel.

Preferably, each support stent independently forms a ring, and each support stent fluctuates to be in a wave shape along the axial direction while extending circumferentially. The support stents have the same structure, and peaks of two adjacent support stents are aligned.

Preferably, with adjacent peaks and valleys of adjacent support stents as connection points, the connector stent is connected to corresponding connection points of two adjacent support stents.

One connector stent is used to connect two adjacent support stents. Preferably, each connector stent independently forms a ring, and each connector stent fluctuates to be in a wave shape along the axial direction while extending circumferentially, and is connected to each connection point at two sides of an extending path to form a closed lattice structure.

When the aortic bare stent is placed vertically, the peaks of the connector stent are connected to the valleys of the upper adjacent support stent, and the valleys of the connector stent are connected to the peaks of the lower adjacent support stent.

The closed lattice structure takes diamonds as unit lattices, and the peaks and the valleys of the connector stent, and the peaks and the valleys of the support stent as connection points.

Preferably, each connector stent independently forms a ring, and each connector stent fluctuates to be in a wave shape along the axial direction while extending circumferentially, part of the peaks and part of the valleys at two sides of an extending path of the connector stent act as connection points to be connected to the connector stent to form an open-loop lattice structure.

Not all of the peaks and valleys of the support stent at two sides of the extending path of the connector stent act as connection points, that is, part of the peaks and the valleys of the support stent exist in isolation, and are not connected to the connector stent.

Further preferably, each connector stent independently forms a ring, and each connector stent fluctuates to be in a wave shape along the axial direction while extending circumferentially, and the peaks and the valleys at two sides of the extending path of the connector stent alternately act as connection points to be connected to the connector stent to form an open-loop lattice structure.

The peaks and the valleys at two sides of the extending path of the connector stent are divided as peaks acting as connection points, peaks not acting as connection points, valleys acting as connection points, and valleys not acting as connection points. The peaks acting as connection points and the peaks not acting connection points are distributed at intervals, and the valleys acting as connection points and the valleys not acting connection points are distributed at intervals.

In the aortic bare stent according to the present disclosure, the support stents and the connector stents are arranged at intervals, and the support stents are at two ends of the bare stent. The number of the peaks and the number of the valleys of each support stent are the same. The number of the peaks and the number of the valleys of the connector stent are the same. Moreover, the support stents and the connector stents have the same number of peaks and the same number of valleys.

In order to ensure the overall radial support strength of the aortic bare stent, the axial length of the support stent is not less than that of the connector stent. Preferably, a ratio of the axial length of the connector stent to the axial length of the support stent falls within a range of 1:1~1:2.5. Further preferably, the ratio of the axial length of the connector stent to the axial length of the support stent falls within a range of 1:1.5~1:2.

In addition to the form in which the support stents and the connector stents independently form rings, the aortic bare stent also may be in other structural forms, for example, except the support stents at positions of head and tail, the support stents at other positions are in an open-loop structure, and adjacent support stents are connected head to tail to form a spiral shape.

Taking 360-degree encircling of the support stent as one turn, two adjacent support stents are connected by the connector stent, and the connector stents on the whole are also in a spiral shape.

Preferably, the connector gent is connected to corresponding connection points in a winding or knotting manner.

The connector stent is in relative fixed connection to corresponding connection points, that is, when the aortic bare stent on the whole is bent, the connector stent is deformed, but the connector stent and the support gent do not slide relatively at the connection points.

In order to avoid a too long axial compression length of the aortic bare stent, preferably, at least one axial connector is further included, and each axial connector is connected to corresponding connection points of the support stent in a knotting or winding manner.

Each axial connector extends along a generatrix of the aortic bare stent, and each axial connector is connected to all or part of the support stents contacting the axial connector.

Since the peaks (or the valleys) of the support stents are aligned, each axial connector is connected sequentially to the peaks (or the valleys) located on the same generatrix of the bare stent.

Preferably, multiple axial connectors are uniformly distributed along a circumferential direction of the aortic bare stent.

In order to satisfy special requirements of different blood vessels, the aortic bare stent according to the present disclosure may be in a tubular shape extending with unequal diameters, for example, the aortic bare stent is in a tapered-tube shape, or the aortic bare stent is in a structure with variable diameters constituted by a tapered-tube shape and a straight-tube shape.

In order to realize the tubular structure extending with unequal diameters for the aortic bare stent, the support stents in the present disclosure have different structures, for example, part of the support stents are in a closed annular structure, part of the support stents are in a net-shape structure, and axial lengths of the support stents are not completely equal. Being adapted to the support stents, the connector stents also may be in different structures.

The present disclosure further provides an aortic dissection stent which includes a covered stent and a bare stent butted with each other, and the bare stent is the aortic bare stent as mentioned.

The covered stent is used to block a proximal tear of a type B dissection, reduce a pressure inside a false lumen, and promote thrombosis of blood inside the false lumen. The aortic bare stent is placed at a distal end of the covered stent, and used to rebuild a true lumen of the blood vessel, and ensure that arterial blood can flow fluently in various internal organs.

Butted portions of the covered stent and the bare stent are nested with each other, that is, at least one portion is an overlapping area. An axial length of the overlapping area is set as required.

The aortic bare stent according to the present disclosure has the proper radial support strength, the proper axial support strength, and the good bending flexibility, and when being released, the aortic bare stent is easy to be bent to be adapted to the form of the blood vessel, thereby reducing the compression to the blood vessel wall.

BRIEF DESCRIPTION OF THE DRAWINGS

FIG. 3b is an enlarged view of a portion A in FIG. 3a.

DETAILED DESCRIPTION

Below the present disclosure is described in detail in combination with the accompanying drawings and embodiments. In the text, a proximal end refers to an end close to a position of heart, and a distal end refers to an end away from the position of heart. In the schematic views of various embodiments, an upper side is the proximal end, and a lower side is the distal end.

Embodiment 1

Figure 1:
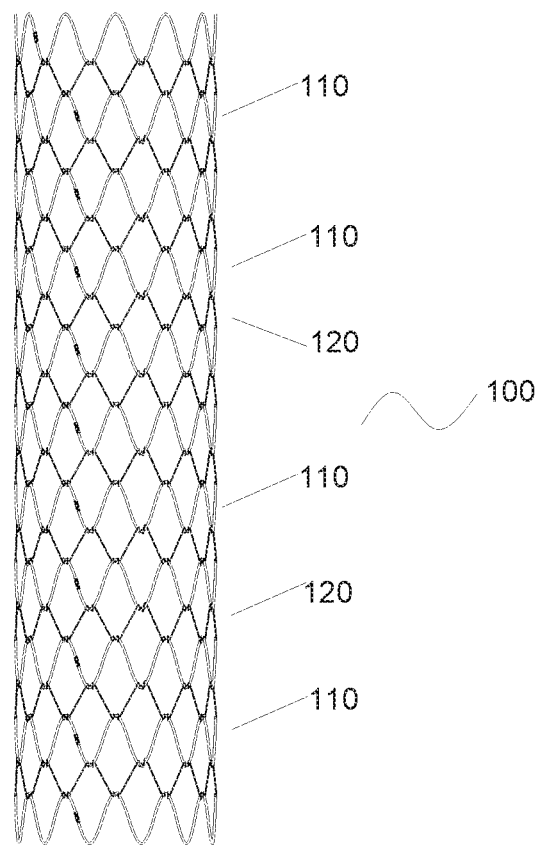
FIG. 1 is a schematic view illustrating an aortic bare stent according to an embodiment 1.

As illustrated in FIG. 1, an aortic bare stent 100 is constituted by multiple annular support stents 110 and multiple annular connector stents 120. The aortic bare stent 100 on the whole is in a tubular net structure, the support stents 110 are in a same structure, and the connector stents 120 are also in a same structure.

The multiple annular support stents 110 are sequentially arranged in parallel at intervals from a proximal end of the aortic bare stent 100 to a distal end of the aortic bare stent 100. One connector stent 120 is arranged between two adjacent support stents 110, that is, the support stents 110 and the connector stents 120 are distributed at intervals along an axial direction of the aortic bare stent 100. In the present embodiment, the support stents 110 and the connector supports 120 have a same diameter, both being 30 mm, that is, a diameter of a tubular shape of the aortic bare stent 100 is 30 mm.

Figure 2A:
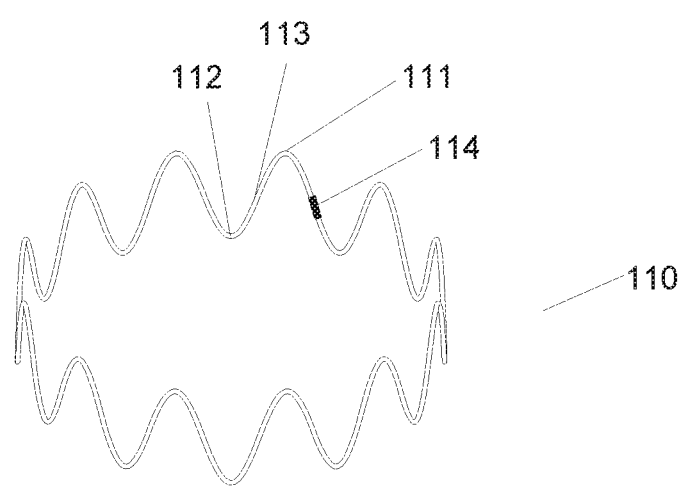
FIG. 2a is a schematic view illustrating a support stent of the aortic bare stent according to the embodiment 1.

As illustrated in FIG. 2a, each support stent 110 extends along a circumferential direction of the aortic bare stent 100, forming a closed annular shape, and fluctuates along the axial direction of the aortic bare stent 100 while extending circumferentially, forming a wave shape.

The wave shape is a sinusoidal waveform (or a cosine waveform). The wave shape has multiple peaks 111 and multiple valleys 112 distributed at intervals. The adjacent peak 111 and valley 112 are connected by a connecting rod 113. The number of the peaks 111 is twelve. The number of the valleys 112 is also twelve. Each support stent 110 has an axial length of 8 mm.

Each support stent 110 is formed by weaving a hyper-elastic nickel titanium wire. The nickel titanium wire has a relatively thin wire diameter falling within a range of 0.2~0.4 mm. Each support stent 110 in the present embodiment is formed by weaving a hyper-elastic nickel titanium wire with a diameter of 0.3 mm.

As illustrated in FIG. 2a, each support stent 110 is provided with one connecting steel jacket 114. Two ends of the hyper-elastic nickel titanium wire are located inside the connecting steel jacket 114, and the two ends of the hyper-elastic nickel titanium wire are fixed inside the steel jacket 114 in a mechanical compressing manner or a welding manner.

Compared with a conventional weaving manner of an aortic covered stent, the hyper-elastic nickel titanium wire having a thinner wire diameter is used in the present embodiment to weave the support stent, and the sinusoidal waveform of each support stent has more peaks and more valleys, such that a support three of the whole aortic bare stent 100 in the circumferential direction is distributed more uniformly, with better flexibility, thus better satisfying requirements of cases with a dissection.

Figure 2B:
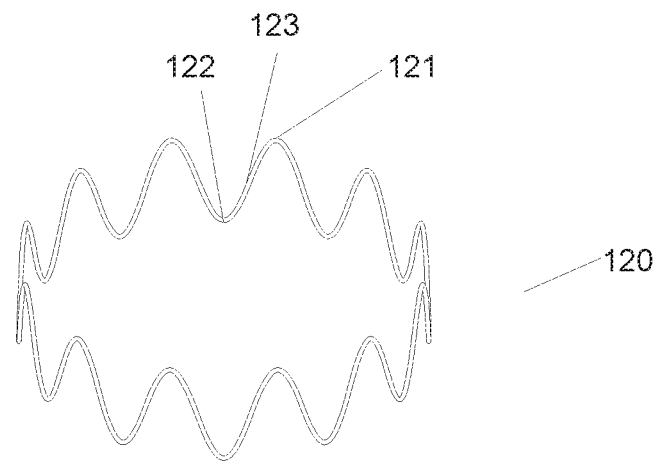
FIG. 2b is a schematic view illustrating a connector stent of the aortic bare stent according to the embodiment 1.

As illustrated in FIG. 2b, each connector stent 120 extends along the circumferential direction of the aortic bare stent 100, forming a closed annular shape, and fluctuates along the axial direction of the aortic bare stent 100 while extending circumferentially, forming a wave shape.

The wave shape is a sinusoidal waveform (or a cosine waveform). The wave shape has multiple peaks 121 and valleys 122 distributed at intervals. The adjacent peak 121 and valley 122 are connected by a connecting rod 123. The number of the peaks 121 is twelve. The number of the valleys 122 is also twelve. Each connector stent 120 has an axial length of 4.5 mm.

Each connector stent 120 is formed by weaving one multi-strand nickel titanium wire. The multi-strand nickel titanium wire is formed by mechanically twisting or weaving no less than three hyper-elastic nickel titanium filaments. The multi-strand nickel titanium wire has a wire diameter falling within a range of 0.1~0.4 mm.

Figure 3A:
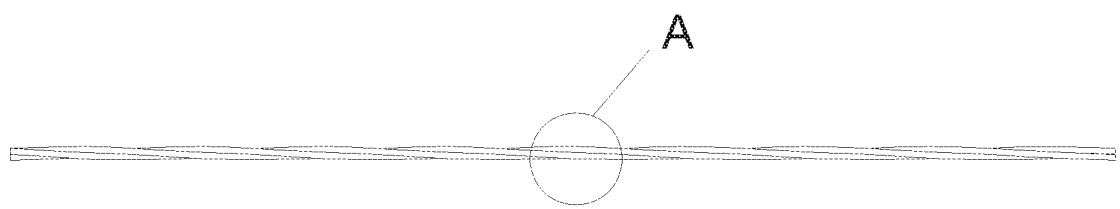
FIG. 3a is a schematic structural view illustrating a multi-strand nickel titanium wire of a dissection bare stent according to the embodiment 1.
Figure 3B:
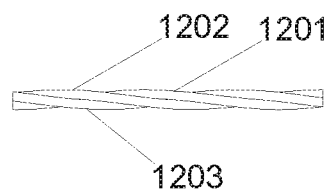

As illustrated in FIG. 3a and FIG. 3b, in the present embodiment, the multi-strand nickel titanium wire is formed by twisting three strands of hyper-elastic nickel titanium monofilaments. The three strands of hyper-elastic nickel titanium monofilaments are a hyper-elastic nickel titanium filament 1201, a hyper-elastic nickel titanium filament 1202, and a hyper-elastic nickel titanium filament 1203, respectively. The three strands of the hyper-elastic nickel titanium monofilaments have a same filament diameter. Each strand of the hyper-elastic nickel titanium monofilament has a filament diameter of 0.07 mm. The twisted multi-strand nickel titanium wire has the wire diameter (a diameter of a circumscribed circle of a cross section) of 0.15 mm. A weaved connector stent 120 is illustrated in FIG. 2b.

Two end portions of the multi-strand nickel titanium wire for fabricating the connector stent 120 are connected together in a knotting manner, in a welding manner or by adding a steel jacket. The two end portions are fixed together in the knotting manner in the present embodiment.

Figure 4:
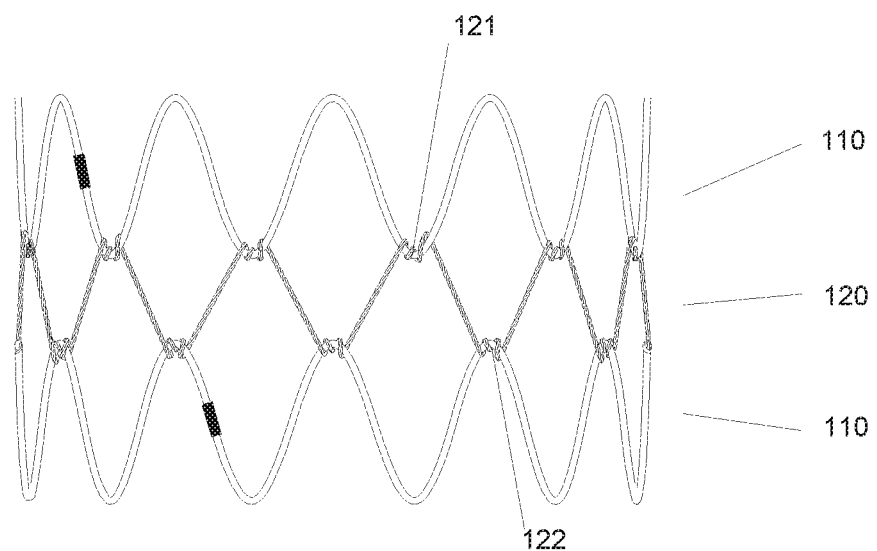
FIG. 4 is a schematic structural view illustrating a connection between the support stent and the connector stent according to the embodiment 1.

As illustrated in FIG. 4, two adjacent support stents 110 are connected by one connector stent 120, the peaks of the two adjacent support stents 110 are arranged in an aligned manner (the valleys are also arranged in an aligned manner). The peaks 121 of each connector stent 120 are connected to the valleys 112 of an upper adjacent support stent 110, and the valleys 122 of each connector stent 120 are connected to the peaks 111 of a lower adjacent support stent 110. All of the support stents 110 and the connector stents 120 are combined to form the aortic bare stent 100 in a tubular shape, and a circumferential face of the tubular shape is in a net structure with diamond grids.

The aortic bare stent 100 according to the present embodiment is formed by connecting and closing eleven support stents 110 and ten connector stents 120, and has a total axial length of 133 mm.

The aortic bare stent 100 provided in the present embodiment has a uniform, reasonable, and relatively small support force on an outer circumferential surface, which not only can avoid a problem of generating new dissection tears due to a too big radial force, but also can ensure a good bending flexibility of the aortic bare stent 100, thus being adapted to various forms of aortic anatomical structures.

The aortic bare stent 100 according to the present embodiment has a relatively good axial support performance in the axial direction, thus avoiding shortening of the stent due to accumulation.

In addition, the aortic bare stent 100 according to the present embodiment is designed in a closed-loop manner, which can avoid a problem of overturn of a single stent caused by an open-loop connection or puncturing of a blood vessel wall by peaks of an open loop.

As illustrated in FIG. 1 and FIG. 4, a single peak 121 or a single valley 122 of each connector stent 120 is fixedly connected together with a single valley 112 or a single peak 111 of a corresponding support stent 110, and the connector stent 120 and the support stent 110 do not move relatively to each other.

Figure 5A:
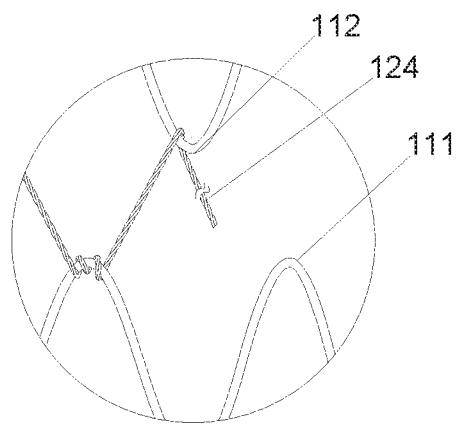
FIG. 5a, FIG. 5b, FIG. 5c, and FIG. 5d are schematic views illustrating a connection manner of winding fixation between the support stent and the connector stent according to the embodiment 1.
Figure 5B:
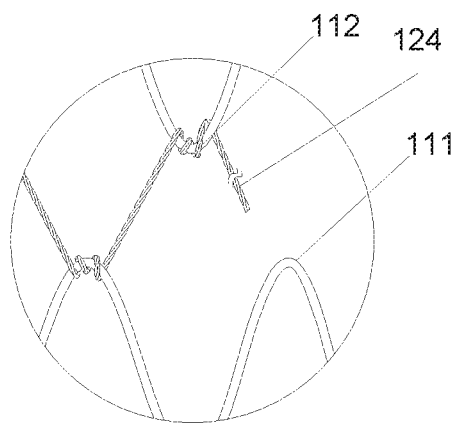

In the present embodiment, each connector stent 120 is fixed, at positions of the peaks or the valleys, on the valleys or the peaks of a corresponding support stent 110 in a winding manner. A process of winding connection is illustrated in FIGS. 5a-5b. The connector stent 120 connects two adjacent support stents 110. When the connector stent 120 is connected to the valleys 112 of the upper support stent 110, a head end 124 of the multi-strand nickel titanium wire goes in from outside of the valley 112 ("outside" refers to outside of the aortic bare stent, and the same interpretation is applied to "outside" and "inside" in the following text, unless otherwise stated), and after winding the valley 112, the head end 124 goes towards the lower support stent 110 and goes to outside of the lower support stent 110, as illustrated in FIG. 5*a*.

The multi-strand nickel titanium wire is wound on the valley of the support stent 110 by 3~5 turns in a manner as illustrated in FIG. 5*a*, three turns in the present embodiment as illustrated in FIG. 5*b*, thus completing fixed winding connection between one peak of the connector stent 120 and the valley 112 of the support stent 110.

Figure 5C:
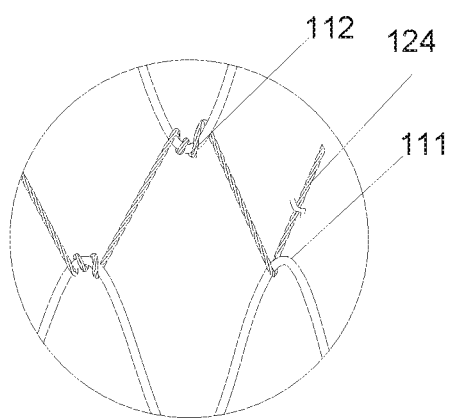

Then, the head end 124 of the nickel titanium wire goes in from outside of the adjacent peak 111 of the lower adjacent support stent 110, and after winding the peak 111, the head end 124 goes towards the upper support stent 110 and goes to outside of the upper support stent 110, as illustrated in FIG. 5*c*.

Figure 5D:
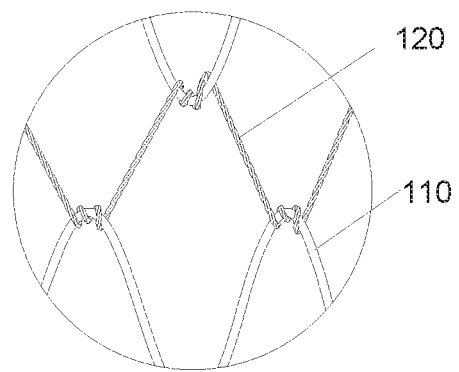

The multi-strand nickel titanium wire is wound on the peak of the support stent 110 by 3~5 turns in a manner as illustrated in FIG. 5*c*, three turns in the present embodiment as illustrated in FIG. 5*d*, thus completing fixed winding connection between one valley of the connector stent 120 and the peak 111 of the support stent 110.

Embodiment 2

Figure 6:
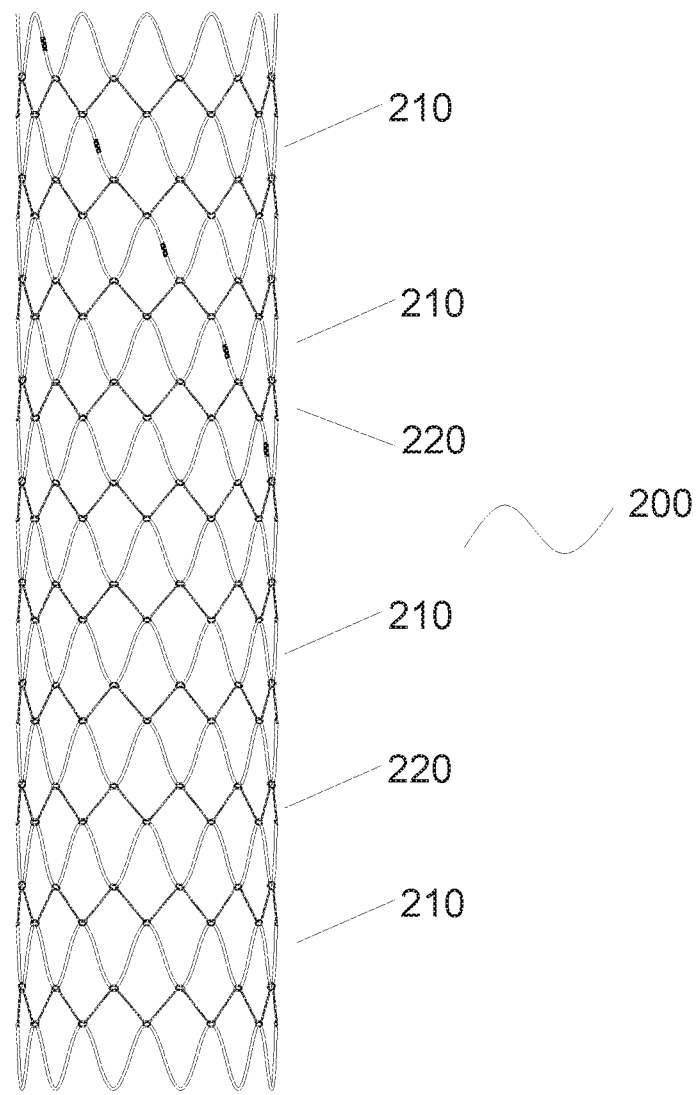
FIG. 6 is a schematic view illustrating a dissection bare stent according to an embodiment 2.

As illustrated in FIG. 6, an aortic bare stent 200 in the present embodiment is constituted by multiple support stents 210 in circles and multiple connector stents 220 in circles. The present embodiment is distinguished from the embodiment 1 merely in that peaks or valleys of the support stents 210 and valleys or peaks of the connector stents 220 are fixed in a knotting manner.

As illustrated in FIG. 7*a*-FIG. 7*e*, in the present embodiment, each connector stent 220 is fixed, at positions of the peaks or the valleys, on the valleys or the peaks of a corresponding support stent 210 in a knotting manner.

Figure 7A:
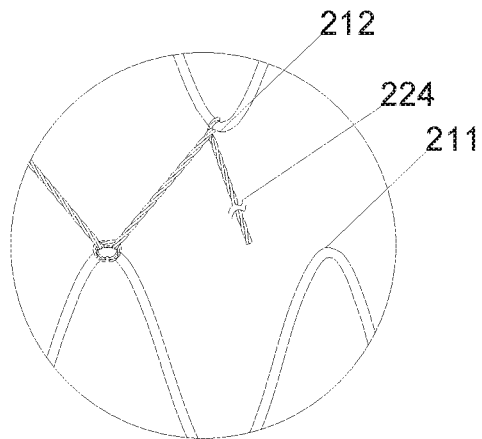
FIG. 7a, FIG. 7b, FIG. 7c, FIG. 7d, and FIG. 7e are schematic views illustrating a connection manner of knotting fixation between a support stent and a connector stent according to the embodiment 2.

As illustrated in FIG. 7*a*, a head end 224 of a multi-strand nickel titanium wire goes out from inside of a valley 212 of an upper support stent, and after winding the valley, passes through a bottom portion of the nickel titanium wire itself.

Figure 7B:
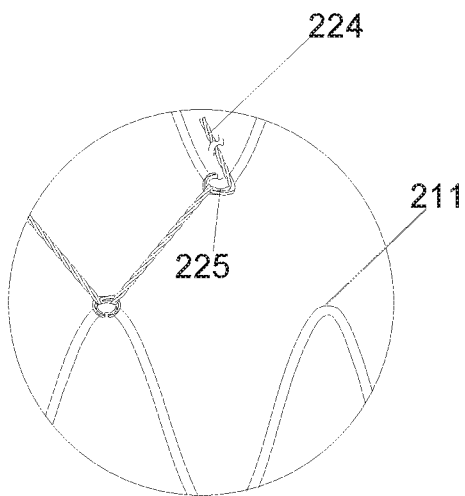
Figure 7C:
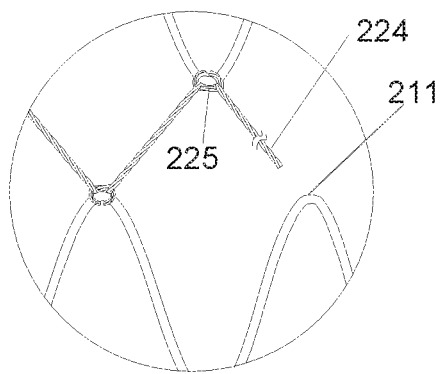

As illustrated in FIG. 7*b*, the head end 224 of the nickel titanium wire goes into inside of the valley from outside of the valley, and a circle 225 is formed between the multi-strand nickel titanium wire and the valley 212 of the support stent 210;

As illustrated in FIG. 7*c*, the head end 224 of the nickel titanium wire winds the valley and goes out from the circle 225 formed by the nickel titanium wire, thus completing the fixed knotting connection between one peak 221 of the connector stent 220 and one valley 212 of the support stent 210.

Figure 7D:
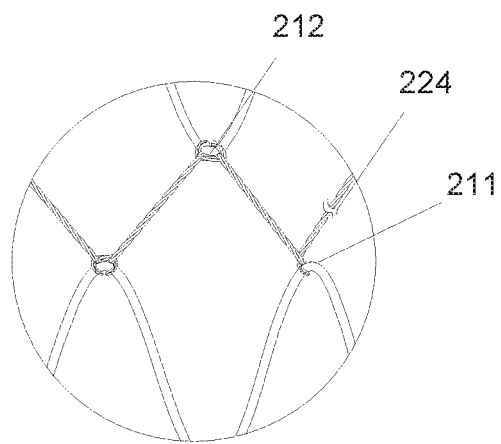
Figure 7E:
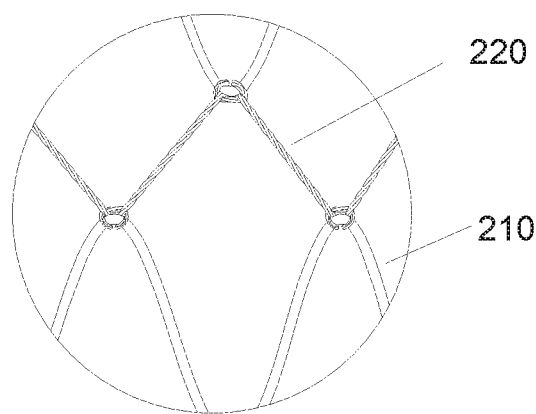

As illustrated in FIG. 7*d* and FIG. 7*e*, the head end 224 of the nickel titanium wire goes out from inside of an adjacent peak 211 of a lower support stent 210, and a fixed knotting connection between the valley 222 of the connector stent 220 and the peak 211 of the lower adjacent support stent 210 is completed in the manner of knotting the peak 221 of the connector stent 220 and the valley 212 of the support stent 210.

Figure 15:
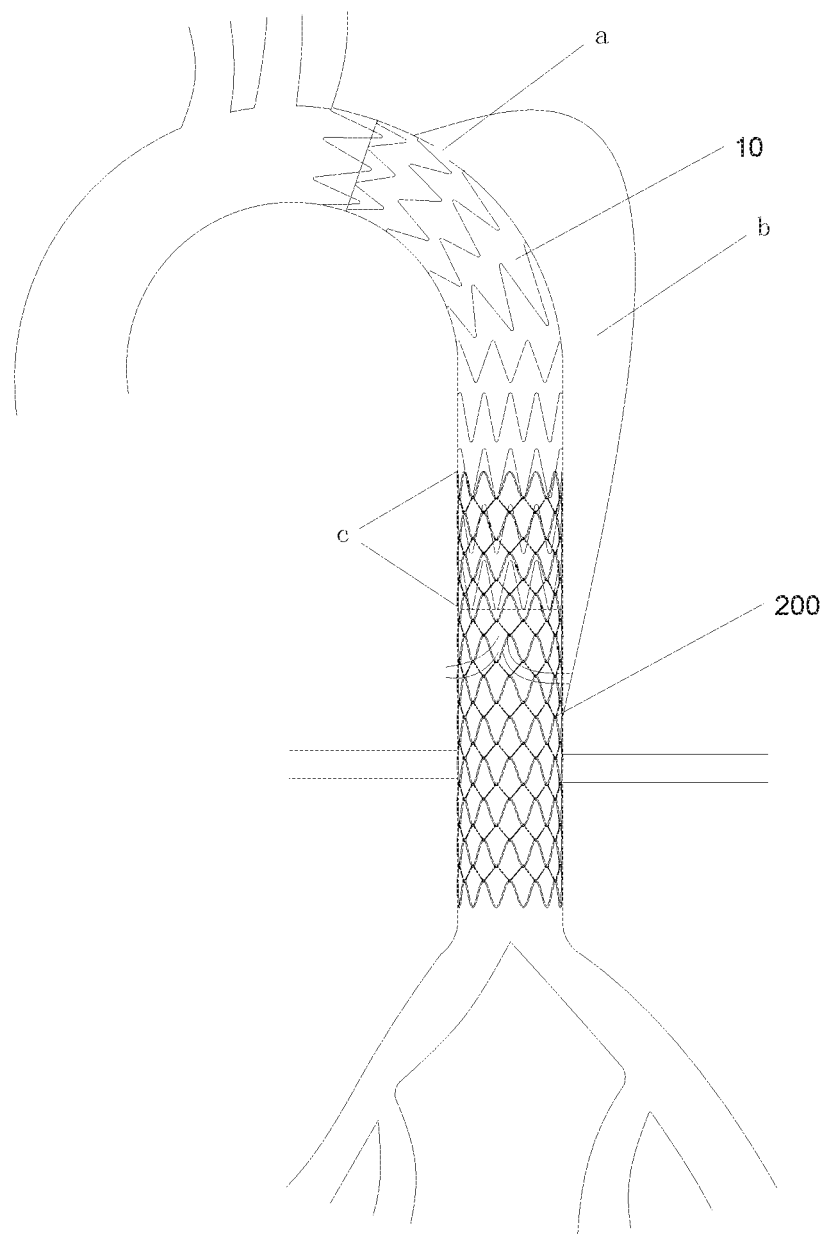
FIG. 15 is a schematic view illustrating use of the aortic bare stent of the embodiment 2 for treatment of an aortic dissection.

FIG. 15 is a schematic view illustrating treatment of a type B aortic dissection with the aortic bare stent 200 provided in the present embodiment in combination with a proximal covered stent 10, In FIG. 1.5, a is a proximal blood vessel tear, b is a false lumen, and c is an overlapping region of the covered stent 10 and the aortic bare stent 200.

The proximal covered stent 10 blocks the proximal tear of the type B dissection, to reduce a pressure inside the false lumen, and promote thrombosis of blood inside the false lumen the aortic bare stent 200 is placed at a distal end of the covered stent 10, and partially overlaps the covered stent 10, for rebuilding the true lumen of the blood vessel, and ensuring that arterial blood flows fluently in various internal organs.

Embodiment 3

The present embodiment is distinguished from the embodiment 2 merely in that the connector stent 220 and the support stent 210 are fixed in a different knotting manner.

As illustrated in FIGS. 8*a*-8*e*, in the present embodiment, each connector stent 220 is fixed, at positions of the peaks or the valleys, on the valleys or the peaks of the corresponding support stent 210 in another knotting manner.

Figure 8A:
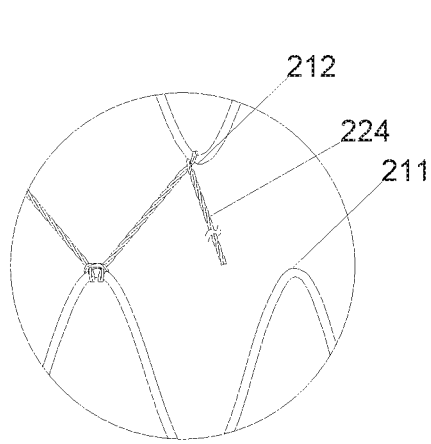
FIG. 8a, FIG. 8b, FIG. 8c, FIG. 8d, and FIG. Se are schematic views illustrating another connection manner of knotting fixation between an annular support stent and an annular connector stent according to an embodiment 3.

As illustrated in FIG. 8*a*, the head end 224 of the multi-strand nickel titanium wire goes in from outside of the valley 212 of the upper support stent 210, and after winding the valley, passes through a top portion of the nickel titanium wire.

Figure 8B:
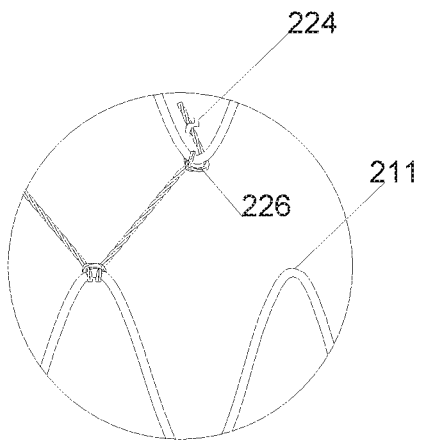

As illustrated in FIG. 8*b*, the head end 224 of the nickel titanium wire goes to outside of the valley from inside of the valley, and a circle 226 is formed between the multi-strand nickel titanium wire and the support stent 210.

Figure 8C:
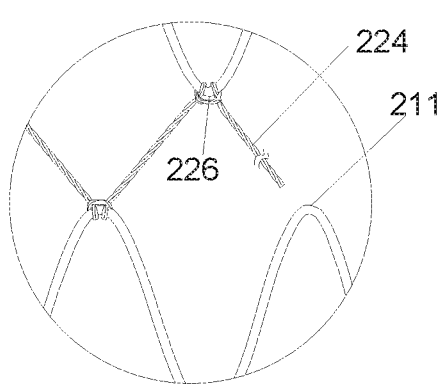

As illustrated in FIG. 8*c*, the head end 224 of the nickel titanium wire winds the valley and goes out from the circle 226 formed by the nickel titanium wire, thus completing the fixed knotting connection between one peak 221 of the connector stent 220 and one valley 212 of the support stent 210.

Figure 8D:
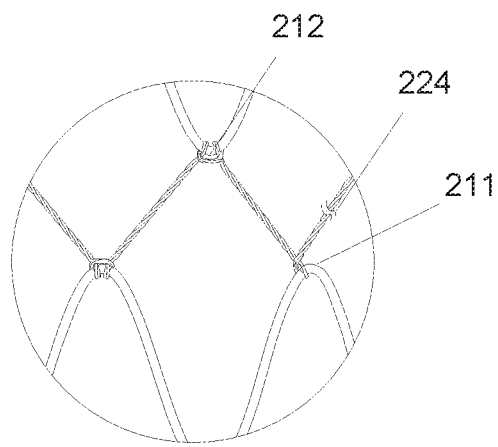
Figure 8E:
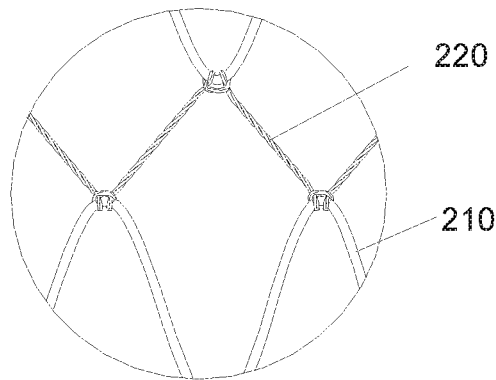

As illustrated in FIG. 8*d*, and FIG. 8*e*, the head end 224 of the nickel titanium wire goes in from outside of an adjacent peak 211 of the lower adjacent support stent 210, and the knotting connection between the valley 222 of the connector stent 220 and the peak 211 of the lower adjacent support stent 210 is completed in the manner of knotting the peak 221 of the connector stent 220 and the valley 212 of the support stent 210.

Embodiment 4

An aortic bare stent 300 according to the present embodiment is distinguished from the embodiment 1 merely in that a dissection bare stent 300 further includes one or more axial connectors 330, in addition to multiple support stents 310 in circles and multiple connector stents 320 in circles.

The number of the axial connectors 330 is a divisor of the number of peaks of each support stent 310. The axial connectors 330 are uniformly distributed on the aortic bare stent 300 in a circumferential direction. Each axial connector 330 connects all or part of annular support stents 310 on a same generatrix of a cylinder in a knotting or winding manner.

Corresponding valleys 312 of the support stents 310 are aligned, and corresponding peaks 311 of the support stents 310 are also aligned. The axial connector 330 connects the valleys 312, or connects the peaks 311.

The axial connectors 330 may be made of one multi-strand nickel titanium wire, and also may be made of a high-strength filament and a mix-woven polymer suture, for example, a PET suture, a PP suture, and so on.

Figure 9:
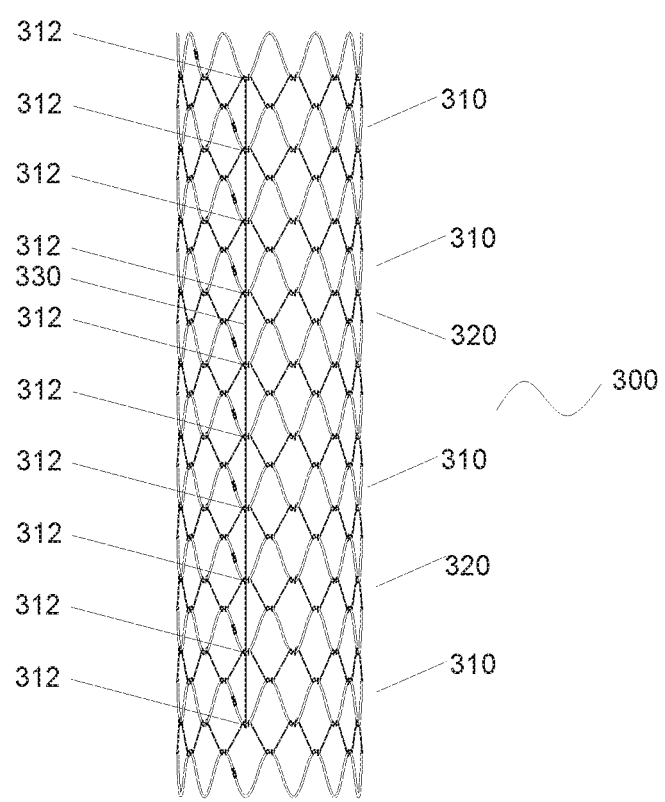
FIG. 9 is a schematic view illustrating a dissection bare stent according to an embodiment 4.

As illustrated in FIG. 9, one axial connector 330 is provided in the present embodiment, and is made of a multi-strand nickel titanium wire with the same structure as the annular connector stent 310, The axial connector 330 is fixedly and sequentially connected to ten valleys 312 of ten proximal support stents on the same generatrix. A connecting manner is the knotting manner as illustrated in the embodiment 3.

A most distal support stent 310 is not fixedly connected to the axial connector 330, and is not restricted by the axial connector 330. By adjusting a length of the axial connector 330 arranged between two adjacent support stents 310, a problem of excessive axial elongation of the aortic bare stent 300 in a sheathing process can be avoided, meanwhile, it also facilitates accurate positioning of the aortic bare stent 300 when being released in a surgical process.

Embodiment 5

Figure 10:
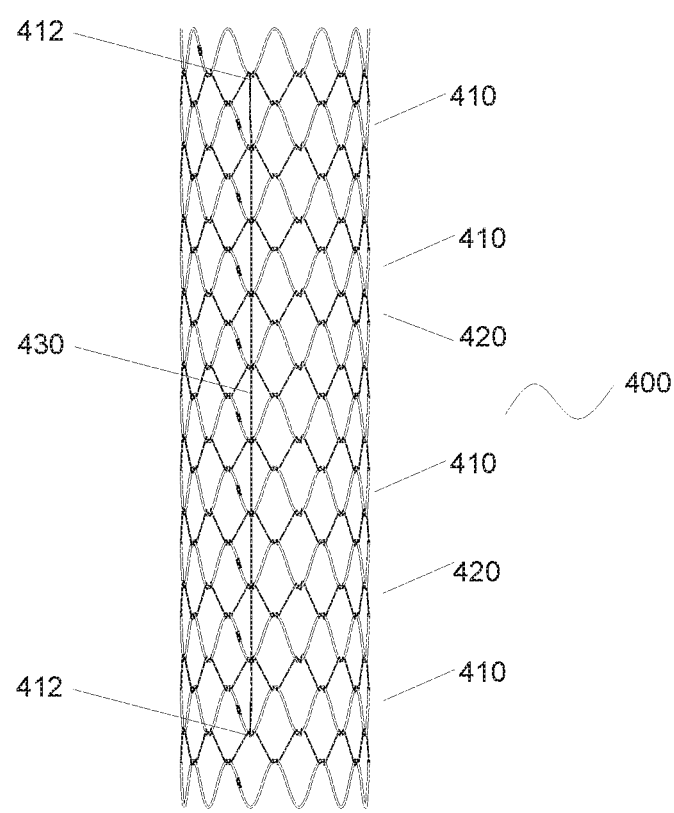
FIG. 10 is a schematic view illustrating a dissection bare stent according to an embodiment 5.

As illustrated in FIG. 10, an aortic bare stent 400 according to the present embodiment is distinguished from the embodiment 4 merely in that the number of valleys of ten proximal support stents 410 connected to an axial connector 430 is different from that of the valleys of ten proximal support stents 310 connected to the axial connector 330.

In the present embodiment, the axial connector 430 is merely fixed in a knotting manner to two valleys 312, namely, a valley 312 of a first support stent 410 and a valley 312 of a tenth support stent 410, on a same generatrix, while second to ninth support stents 410 are not fixedly connected to the axial connector 430.

Embodiment 6

Figure 11A:
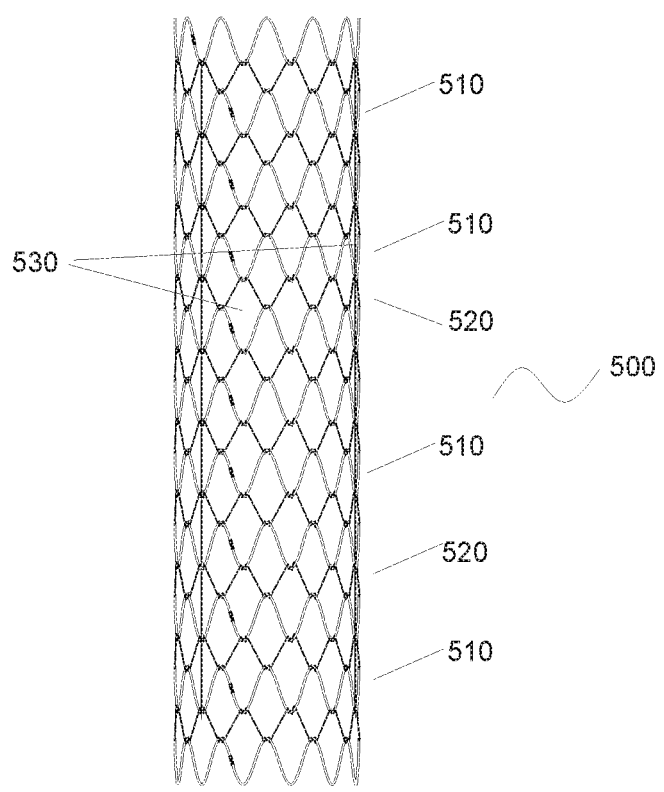
FIG. 11a is a front view illustrating a dissection bare stent according to an embodiment 6.
Figure 11B:
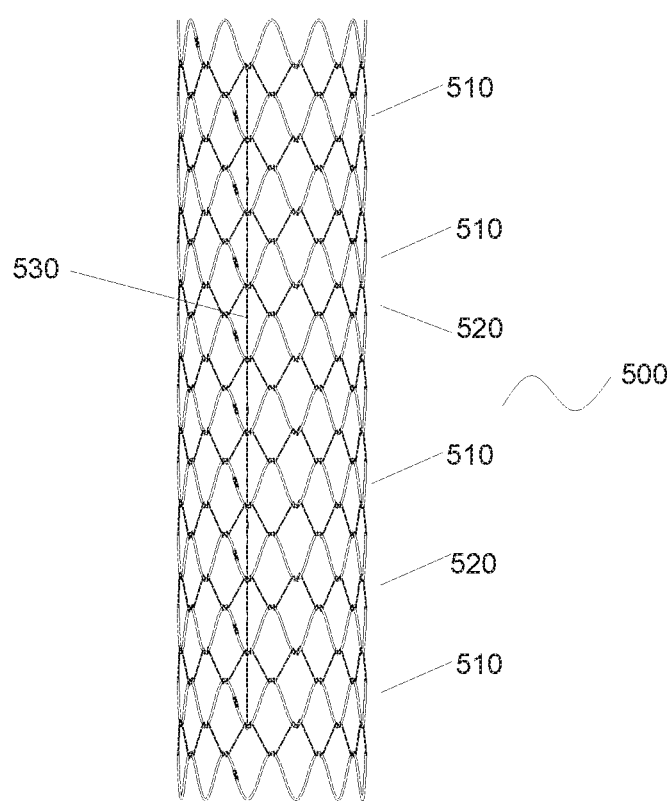
FIG. 11b is a rear view illustrating a dissection bare stent according to the embodiment 6.

As illustrated in FIG. 11a and FIG. 11b, an aortic bare stent 500 according to the present embodiment is distinguished from the embodiment 4 merely in the following: three axial connectors 530 are provided in the present embodiment, the three axial connectors 530 are uniformly distributed in a circumferential direction of the aortic bare stent 500, and each axial connector 530 is connected to valleys of support stents 510 in a same manner as illustrated in the embodiment 4.

Embodiment 7

Figure 12:
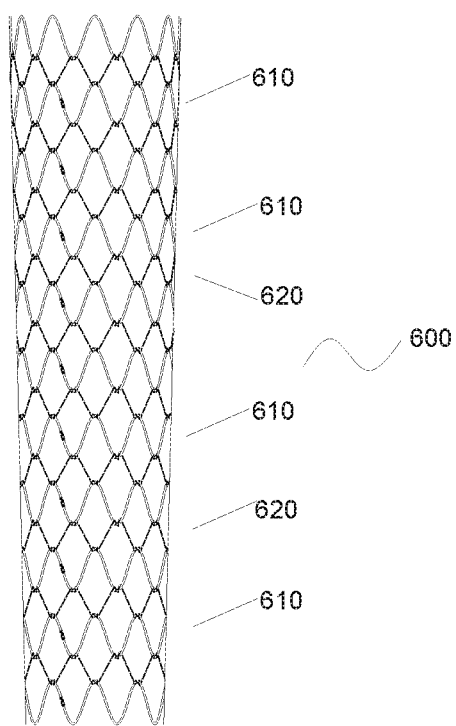
FIG. 12 is a schematic view illustrating a dissection bare stent according to an embodiment 7.

As illustrated in FIG. 12, an aortic bare stent 600 according to the present embodiment is constituted by multiple support stents 610 in circles and multiple connector stents 620 in circles.

The present embodiment is distinguished from the embodiment 1 merely in that the aortic bare stent 600 according to the present embodiment is in a tapered-tube-shape structure, and a proximal end of the aortic bare stent 600 has a diameter of 30 mm, a distal end of the aortic bare stent 600 has a diameter of 26 mm, and the aortic bare stent 600 has an axial length of 180 mm.

Embodiment 8

Figure 13:
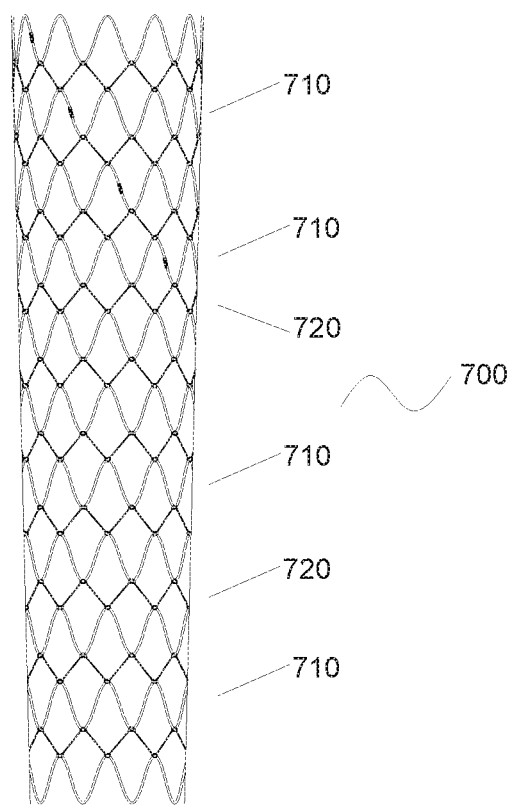
FIG. 13 is a schematic view illustrating a dissection bare stent according to an embodiment 8.

As illustrated in FIG. 13, an aortic bare stent 700 according to the present embodiment is constituted by multiple support stents 710 in circles and multiple connector stents 720 in circles.

The present embodiment is distinguished from the embodiment 2 merely in the following: the aortic bare stent 700 according to the present embodiment is in a tapered-tube-shape structure, and a proximal end of the aortic bare stent 700 has a diameter of 30 mm, a distal end of the aortic bare stent 700 has a diameter of 26 mm, and the aortic bare stent 700 has an axial length of 180 mm.

Embodiment 9

Figure 14:
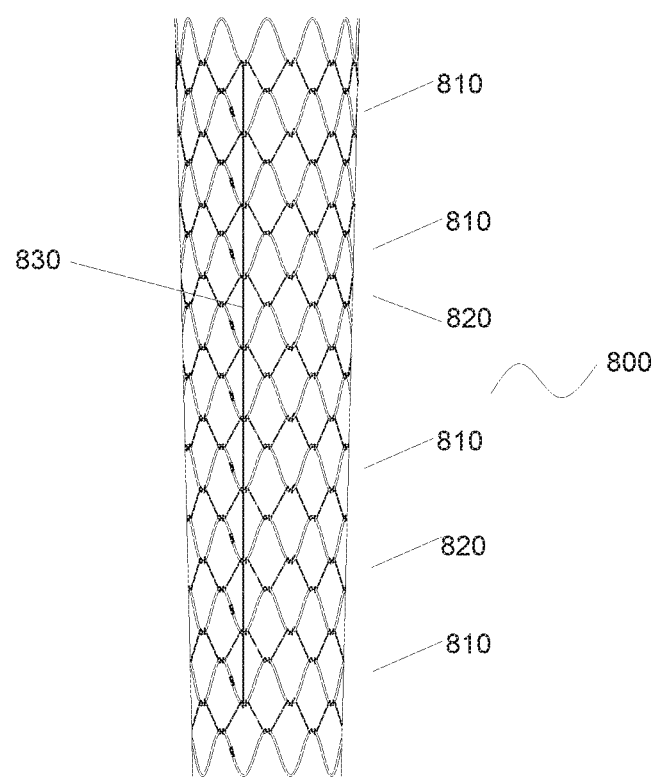
FIG. 14 is a schematic view illustrating a dissection bare stent according to an embodiment 9.

As illustrated in FIG. 14, an aortic bare stent 800 according to the present embodiment is constituted by multiple support stents 810 in circles, multiple connector stents 820 in circles, and an axial connector 830.

The present embodiment is distinguished from the embodiment 4 merely in the following: the aortic bare stent 800 according to the present embodiment is in a tapered-tube-shape structure, and a proximal end of the aortic bare stent 800 has a diameter of 30 mm, a distal end of the aortic bare stent 800 has a diameter of 26 mm, and the aortic bare stent 800 has an axial length of 180 mm.

Embodiment 10

Figure 16:
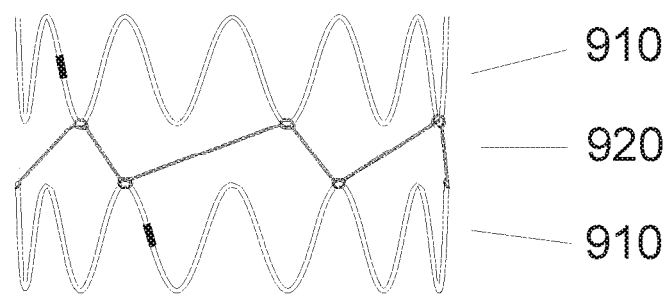
FIG. 16 is a schematic view illustrating a dissection bare stent according to an embodiment 10.

As illustrated in FIG. 16, an aortic bare stent 900 according to the present embodiment is constituted by multiple support stents 910 in circles and multiple connector stents 920 in circles.

The present embodiment is distinguished from the embodiment 2 merely in that connection points for the support stents 910 and the connector stents 920 are different in the present embodiment.

As illustrated in FIG. 16, among valleys of the upper support stent 910 adjacent to the connector stent 920, each two connection points are spaced by one valley which does not act as a connection point, likewise, among peaks of the lower support stent 910 adjacent to the connector stent 920, each two connection points are spaced by one peak which does not act as a connection point.

What is claimed is:

1. An aortic bare stent, in a tubular net structure, comprising:
   a plurality of support stents, wherein the plurality of support stents are arranged along an axial direction, each of the plurality of support stents independently forms a ring, and each of the plurality of support stents is made of a single-strand nickel titanium wire; and
   a plurality of connector stents, wherein each of the plurality of connector stents is operable to connect two adjacent support stents among the plurality of support stents, each of the plurality of connector stents is made of multi-strand nickel titanium filaments, a diameter of each of the plurality of connector stents is the same as that of each of the plurality of support stents, and a flexural rigidity of each of the plurality of connector stents is less than that of each of the plurality of support stents.

2. The aortic bare stent of claim 1, wherein the multi-strand nickel titanium filaments are twisted or weaved to form a multi-strand composite wire for constructing each connector stent, and the single-strand nickel titanium wire has a larger diameter than each nickel titanium filament for constructing each connector stent.

3. The aortic bare stent of claim 1, wherein a ratio of the flexural rigidity of each of the plurality of connector stents to the flexural rigidity of each of the plurality of support stents falls within a range of 0.5:100~20:100.

4. The aortic bare stent of claim 1, wherein each of the plurality of support stents fluctuates to be in a wave shape along the axial direction while extending circumferentially, and peaks of each two support stents connected to a same connector stent are aligned.

5. The aortic bare stent of claim 4, wherein with adjacent peaks and valleys of each two support stents connected to a same connector stent as connection points, each connector stent is connected to corresponding connection points of two support stents connected to the connector stent.

6. The aortic bare stent of claim 5, wherein each of the plurality of connector stents independently forms a ring, and each of the plurality of connector stents fluctuates to be in a wave shape along the axial direction while extending circumferentially, and is connected to each connection point at two sides of an extending path to form a closed lattice structure.

7. The aortic bare stent of claim 5, wherein each of the plurality of connector stents independently forms a ring, and each of the plurality of connector stents fluctuates to be in a wave shape along the axial direction while extending circumferentially, part of peaks and part of valleys at two sides of an extending path of each of the plurality of connector stents act as connection points to be connected to each of the plurality of connector stents to form an open-loop lattice structure.

8. The aortic bare stent of claim 5, wherein each of the plurality of connector stents is connected to corresponding connection points in a winding manner.

9. The aortic bare stent of claim 2, wherein each nickel titanium filament has a diameter falling within a range of 0.05~0.2 mm.

10. The aortic bare stent of claim 1, wherein a ratio of an axial length of each of the plurality of connector stents to an axial length of each of the plurality of support stents falls within a range of 1:1~1:2.5.

11. The aortic bare stent of claim 1, further comprising at least one axial connector, each of the at least one axial connector being connected to corresponding connection points of each of the plurality of support stents in a knotting or winding manner.

12. The aortic bare stent of claim 11, wherein each of the at least one axial connector is connected to all or part of the plurality of support stents contacting the axial connector.

13. The aortic bare stent of claim 11, wherein multiple axial connectors are distributed uniformly along a circumferential direction of the aortic bare stent.

14. An aortic dissection stent, comprising:
a covered stent; and
an aortic bare stent in a tubular net structure and butted with the covered stent, comprising:
 a plurality of support stents, wherein the plurality of support stents are arranged along an axial direction, each of the plurality of support stents independently forms a ring, and each of the plurality of support stents is made of a single-strand nickel titanium wire; and
 a plurality of connector stents, wherein each of the plurality of connector stents is operable to connect two adjacent support stents among the plurality of support stents, each of the plurality of connector stents is made of multi-strand nickel titanium filaments, a diameter of each of the plurality of connector stents is the same as that of each of the plurality of support stents, and a flexural rigidity of each of the plurality of connector stents is less than that of each of the plurality of support stents.

15. The aortic dissection stent of claim 14, wherein and each of the plurality of support stents fluctuates to be in a wave shape along the axial direction while extending circumferentially, and peaks of each two support stents connected to a same connector stent are aligned.

16. The aortic dissection stent of claim 15, wherein with adjacent peaks and valleys of each two support stents connected to a same connector stent as connection points, each connector stent is connected to corresponding connection points of two support stents connected to the connector stent.

17. The aortic dissection stent of claim 16, wherein each of the plurality of connector stents independently forms a ring, and each of the plurality of connector stents fluctuates to be in a wave shape along the axial direction while extending circumferentially, and is connected to each connection point at two sides of an extending path to form a closed lattice structure.

18. The aortic dissection stent of claim 16, wherein each of the plurality of connector stents independently forms a ring, and each of the plurality of connector stents fluctuates to be in a wave shape along the axial direction while extending circumferentially, part of peaks and part of valleys at two sides of an extending path of each of the plurality of connector stents act as connection points to be connected to each of the plurality of connector stents to form an open-loop lattice structure.

19. The aortic dissection stent of claim 14, further comprising at least one axial connector, each of the at least one axial connector being connected to corresponding connection points of each of the plurality of support stents in a knotting or winding manner.

20. The aortic bare stent of claim 5, wherein each of the plurality of connector stents is connected to corresponding connection points in a knotting manner.

* * * * *